(12) United States Patent
Burt et al.

(10) Patent No.: US 6,743,900 B2
(45) Date of Patent: Jun. 1, 2004

(54) PROTEOSOME INFLUENZA VACCINE

(75) Inventors: David S. Burt, Ormeaux (CA); David Hugh Jones, Baie D'Urfe (CA); George H. Lowell, Hampstead (CA); Gregory Lee White, Montreal (CA); Kirkor Torossian, Verdun (CA); Louis F. Fries, III, Columbia, MD (US); Martin Plante, Montreal (CA)

(73) Assignee: ID Biomedical Corporation of Quebec, Ville St. Laurent (CA)

( * ) Notice: Subject to any disclaimer, the term of this patent is extended or adjusted under 35 U.S.C. 154(b) by 0 days.

(21) Appl. No.: 09/788,280

(22) Filed: Feb. 15, 2001

(65) Prior Publication Data

US 2001/0053368 A1 Dec. 20, 2001

Related U.S. Application Data

(60) Provisional application No. 60/182,476, filed on Feb. 15, 2000.

(51) Int. Cl.[7] .................................................. A23J 1/00
(52) U.S. Cl. ................. 530/414; 424/204.1; 424/206.1; 424/234.1; 424/249.1; 530/300; 530/350; 530/412
(58) Field of Search ............................ 424/184.1, 185.1, 424/193.1, 197.11, 199.1, 203.1, 210.1, 249.1, 250.1, 204.1, 206.1, 234.1; 435/69.1, 69.3, 69.7, 320.1; 530/300, 305, 350, 395, 402, 412, 825, 826, 414

(56) References Cited

U.S. PATENT DOCUMENTS

| | | | |
|---|---|---|---|
| 4,707,543 A | 11/1987 | Zollinger et al. | 530/402 |
| 5,716,637 A | 2/1998 | Anselem et al. | 424/450 |
| 5,726,292 A | 3/1998 | Lowell | 530/403 |
| 5,961,970 A | 10/1999 | Lowell et al. | 424/93.1 |
| 5,985,284 A | 11/1999 | Lowell | 424/234.1 |
| 6,476,201 B1 | 11/2002 | Lowell et al. | 530/414 |

FOREIGN PATENT DOCUMENTS

| | | |
|---|---|---|
| WO | WO 95/11700 | 5/1995 |
| WO | WO 97/10844 | 3/1997 |
| WO | WO 98/01558 | 1/1998 |

OTHER PUBLICATIONS

Lowell, G.H. (1990). In: *New Generation Vaccines.*, G.C. Woodrow and M.M. Levine eds., Marcel Dekker, Inc., New York, p. 141–160; 325–348.
Lowell, et al. (1995). *Journal of cell biochem* S19A.
Lowell, et al. (1995). *American Soc for microlbio. 2nd Nat Conf.* p. 81.
Lowell, et al. (1996). *Infec & Imm* 64(5):1706–1713.
Lowell, et al. (1996). *Infec& Imm* 64(11):4686–93.
Lowell, et al. (1997). *Journal of infecious diseases* 175(2):292–301.
Mallett, C.P., Lowell, G.H. et al. (1995). *Infect. Immun.*63:2382–2386.
Orr, N., Lowell, G.H. et al. (1993). *Infect. Immun.* 61:2390.
Barchfield, et al., *Vaccine* (1999) 17:695–704.
Benyedidia et al., Letters in Peptide Science (1998) 5(5–6):341–344.
Berstad et al., *Vaccine* (2000) 18:1910–1919.
Dalseg, R., et al., *Vaccines* (1999) 17:2336–2345.
Gluck, et al., *J. Infect. Dis.* (2000) 181:1129–1132.
Hashigucci, et al., *Vaccine* (1996) 14:113–119.
Levi, R., et al., *Vaccine* (1995) 13:1353–1359.
Lowell, G.H., et al., *J. Exp. Med.* (1988) 167:658–663.
Lowell, G.H., et al., *Science* (1988) 240:800–802.
Lowell, G.H., in "New Generation Vaccines" 2nd ed., Marcel Dekker, Inc. New York, Basil, Hong Kong (1997) pp. 193–206.
Lynch, E.C., et al., *Biophys. J.* (1984) 45:104–107.
McGhee, et al., *J. Immunol.* (2000) 165:4778–4782.
Plante et al., Abstracts of the General Meeting of the American Society for Microbiology (2000) 100:297.
Slavik et al., Database accession No. 131:57769, XP002174983 (1998).
Slavik et al., *Acta Virologica* (1993) 37(6):449–458.
Tamura, et al., *J. Immunol.* (1992) 149:981–988.

*Primary Examiner*—Ulrike Winkler
(74) *Attorney, Agent, or Firm*—Townsend and Townsend and Crew LLP

(57) ABSTRACT

Improved forms of vaccines which comprise proteosomes and protein antigens are described. Vaccines which contain influenza HA as the antigen are used for illustration as to demonstrate efficacy. Improvements in the preparation of the vaccines themselves and the proteosome component are also included.

17 Claims, 7 Drawing Sheets

A. Serum HAI

B. Nasal sIgA

PROTEOSOME INFLUENZA VACCINE

This application claims priority from U.S. Serial No. 60/182,476 filed Feb. 15, 2000, the contents of which are incorporated herein by reference.

FIELD OF THE INVENTION

The invention is in the field of vaccine preparation. New and improved techniques are illustrated for the preparation of a vaccine against influenza, which techniques are applicable to protein-based vaccines generally.

BACKGROUND OF THE INVENTION

Flue Incidence

Vaccination is the most effective way of reducing the high morbidity and mortality rates as well as diminishing the enormous social and economic impact associated with influenza infection. Although detergent-containing split influenza vaccines are available, the level of vaccination compliance especially in the high-risk groups such as infants and the elderly is low. For example, it is estimated that less than half of the eligible population over the age of 65 actually receives the vaccine. In addition, despite being 70–90% effective in inducing immunity in healthy adults, the current injectable influenza vaccines are poorly immunogenic as a single dose in infants and the geriatric population. Seroconversion rates as low as 20–50% have been reported amongst the elderly. This reduced response in the elderly is believed due to a decline in the Type 1 T cell response, including cytotoxic T lymphocyte activity in this age group. The combination of reduced compliance and poor immunogenicity ensures that large sectors of the general population remain at high risk of infection and complications caused by influenza. Numerous efforts to enhance the immunogenicity of injectable influenza subunit vaccines by co-administering them with adjuvants have proved unsuccessful due to unacceptable rates of local reactogenicity following immunization and the inability to reproduce the strong immunostimulatory effects seen in animal models in humans.

Advantages of Nasal Vaccines

Since influenza infections are restricted to the upper and lower respiratory tracts, nasally-delivered influenza vaccines offer a more benign approach to vaccination that should increase immunization compliance in all ages of the population. Furthermore, immunization by the nasal route may be more effective compared with intramuscular injection because the production of local secretory IgA in the upper respiratory tract can protect against influenza infection, while injectable influenza vaccines are inefficient at inducing mucosal IgA. Influenza specific secretory IgA shows a broader cross-reactivity for variant strains of virus and thus may offer a greater degree of protection against mutant influenza viruses. In particular, nasal flu vaccines may be more effective in the elderly since, unlike the systemic immune system, mucosal immune responses do not deteriorate with age. Nasal flu vaccines that also stimulate systemic immune responses may protect the lower respiratory tract (lungs) due to transudation of antibodies from the serum. In addition, influenza-specific cytotoxic T cells (CTL) in nasal associated lymphoid tissue can contribute to recovery from infection.

Live attenuated cold adapted (CAV) influenza vaccines conventionally have been used via the nasal route in humans. These influenza strains are genetic reassortants combining the HA and NA genes of the current strains of flu virus with the 6 genes encoding the other internal and structural proteins from an influenza donor virus adapted to grow at lower temperatures (25° C.) thereby allowing only minimal replication in the nasopharyngal respiratory tract. These vaccines have the advantage of inducing protective immune responses similar to those elicited by natural infection with influenza, including induction of secretory IgA in the nasal washes, interferon gamma production in restimulated PMNC's and activation of CTL specific for internal viral proteins that may broaden the cross-reactivity against viruses within the same sub-type. CAV influenza vaccines are close to commercialization and have been demonstrated to be well-tolerated and immunogenic in children and healthy adults. In recent studies in healthy children, one or two doses of CAV flu vaccine have been shown to induce equivalent systemic antibody as injectable split flu vaccines. The ability of a single dose of CAV to induce >80% protection in seronegative children is an advantage over injectable split vaccines that require two immunizations to achieve similar protection in this age group. While preexisting circulating antibodies in healthy adults and the elderly prevent efficient seroconversion in these age groups (see below), CAV's have been demonstrated to significantly reduce the number of febrile illnesses, days lost at work and visits to healthcare providers compared with placebo. In the elderly, CAV's in combination with an injectable split subunit vaccine significantly reduced laboratory documented influenza compared to placebo.

Despite the benefits of described above CAV vaccines for influenza have a number of drawbacks: healthy adults and the elderly who have been previously exposed to influenza viruses respond poorly to CAV vaccines and often do not reach the levels of serum hemagglutination inhibition (HAI) activity that correlate with protection. This is particularly significant for the elderly who are amongst the highest risk group and currently the only group where global vaccination is advised. In addition, due to the potential problems with reversion to wild-type stains and/or recombination with circulating strains, CAV's are not recommended for use in immunosuppressed or pregnant women. Despite 20 years of clinical evaluation of CAV influenza vaccines licensing has been delayed due to production and quality control issues.

In order to circumvent the potential safety concerns with CAV influenza vaccines, there are currently attempts to develop nasal inactivated "split" influenza vaccines (ISIV). Inactivated split influenza vaccines contain purified influenza hemagglutinin (HA). Inactivated split influenza vaccines given alone or with various particulate delivery vehicles or enterotoxin-based adjuvants have induced influenza specific mucosal and systemic immune responses in animals and humans.

Nasal Formulation of ISIV

At doses equivalent to those given via the injectable route, nasal ISIV containing antigen alone reproducibly induce significantly higher levels of nasal IgA in animals and in limited studies in humans. However, two or more doses of nasal ISIV at higher amounts of HA are required to induce levels of serum HAI equivalent to injectable ISIV which make such vaccines less viable commercially.

Enterotoxin Addition

Increased influenza specific mucosal and serum immune responses can be achieved in mice by administering ISIV nasally with enterotoxins such as cholera toxin B subunit (CTB) Tamura, et al., *J. Immunol.* (1992) 149:981–988 (which contained a significant amount of active cholera toxin even if referred to as CTB, since a recombinant source of CTB was not used in these studies) and recombinant heat-labile toxin from *E. coli*(rLT), Barchfield, et al., *Vaccine* (1999) 17:695–704.

In mice these enterotoxins are powerful mucosal adjuvants that are capable of inducing both enhanced secretory IgA and serum immune responses against associated antigens including inactivated split influenza vaccine. Recombinant LT was also shown to enhance the local and systemic HA specific response against ISIV in humans (Hashigucci, et al., *Vaccine* (1996) 14:113–119). However, the evaluation of enterotoxin-based adjuvants nasally in humans has been halted by the US FDA due to the results from pre-clinical toxicity studies in mice, showing that the enterotoxins reach the olfactory bulb region of the CNS and induce strong inflammatory reactions in that tissue following nasal administration. This finding has significantly hampered development of flu vaccines with these adjuvants (McGhee, et al., *J. Immunol.* (2000) 165:4778–4782) and would likely preclude the use of this type of adjuvant in human vaccines for the foreseeable future.

Lipid Based Formulations

Particulate species such as the virosome (a liposome formulation with influenza antigens) have also been tested in animal studies and in humans as effective nasal delivery vehicles for inactivated influenza antigens. Particulate antigens may enhance uptake by antigen presenting cells in nasal associated lymphoid tissue. Virosomes are liposomes containing influenza virus antigens associated with spheres consisting of lipids. These vaccines have been licensed in Europe as injectables. In mice, nasal virosomes induce serum titers to the same levels as equivalent amounts of injectable split antigen together with significantly higher levels of mucosal secretory IgA. Virosomes have been also shown to be immunogenic in humans following nasal immunization, however in two clinical trials it was demonstrated that recombinant LT was necessary to achieve specific titers of serum antibody equivalent to injectable vaccine following nasal immunization with 30 µg total HA given in two doses (Gluck, et al., *J. Infect. Dis.* (2000) 181:1129–1132). Although currently licensed in Switzerland, the requirement for the potentially neurotoxic rLT to achieve immunogenic equivalency with injectable flu vaccines precludes the vaccine in many territories including North America.

Another particulate delivery vehicle under development is the Biovector system that comprises an inner core of carbohydrate surrounded by lipid envelope. In clinical studies, nasal ISIV together with Biovectors demonstrated higher serum HAI and mucosal IgA compared with placebo. However, two doses of the highest level tested of influenza antigen with Biovectors elicited an increase HAI titers that were not significant enough to warrant continued development of this product by a major vaccine manufacturing partner who discontinued cooperative involvement with this technology after examining the data, suggesting the need to supplement the Biovectors with an immunostimulant to achieve the levels of serum HAI that correlate with protection.

ISIV formulated with MF59, a lipid based emulsion, has not elicited responses significantly different enough from control influenza articles to warrant continued development. Another technology, monophosphoryl lipid A (MPLA), is a lipoplysachharide adjuvant consisting of oil-based or aqueous formulations of a lipid isolated from the lipopolysaccharide of *Salmonella minnesota* R595. This technology has also been used in mice to make nasal influenza vaccines with moderate success in pre-clinical studies.

Proteosome Technology

"Proteosome" has been used to describe preparations of outer membrane proteins of Meningococci and similar preparations from other bacteria. Lowell, G. H., et al, *J. Exp. Med.* (1988) 167:658–663; Lowell, G. H., et al., *Science* (1988) 240:800–802; Lynch, E. C., et al., *Biophys. J.* (1984) 45:104–107; U.S. Pat. No. 5,726,292 issued Mar. 10, 1998; U.S. Pat. No. 4,707,543 issued Nov. 17, 1987. The use of proteosomes for formulation of vaccines has been reviewed by Lowell, G. H., in "New Generation Vaccines" 2nd ed., Marcel Dekker, Inc., New York, Basil, Hong Kong (1997) pages 193–206, the contents of which are incorporated herein by reference. Proteosomes are described as comparable in size to certain viruses which are hydrophobic and safe for human use. Proteosomes are said to be useful in formulating vaccines with a variety of proteins and peptides. The review describes formulation of compositions comprising non-covalent complexes between various antigens and proteosomes which are formed when solubilizing detergent is selectively removed using exhaustive dialysis technology. With respect to the bacterial shigella vaccine, ultrafiltration was reported to be successful. Vaccines wherein the antigens are shigella lipopolysaccharide, Brucella lipopolysaccharide, Staphylococcal enterotoxin B toxoid, human immunodeficiency virus envelope protein, *E. coli* pilus adhesion proteins, and various peptides such as those derived from rice and influenza virus. These formulations are intended for mucosal application. Parenteral vaccines were also formulated. In particular, peptides derived from influenza (not the entire antigen) were used in vaccine preparation. Levi, R., et al., *Vaccine* (1995) 13:1353–1359. An additional description of outer membrane vesicles from Meningococcus acting as mucosal adjuvants for influenza virus antigens is described by Dalseg, R., et al., *Vaccines* (1998) 96:177–182.

Despite the multiplicity of efforts to formulate successful vaccines, there remains a need for efficient methods and effective compositions to immunize individuals, particularly against infection by influenza.

DISCLOSURE OF THE INVENTION

The present invention describes proteosome-influenza vaccine compositions and processes for their production. These vaccines are straightforward to produce and are able to protect against influenza infection. A preferred embodiment is a nasal proteosome influenza vaccine that contains inactivated influenza antigens, preferably HA, non-covalently formulated with proteosomes formed from the purified outer membrane proteins of gram negative bacteria such as *Neisseria meningitides*. Although vaccines directed against influenza are exemplified herein, the processes employed are useful generally in preparing vaccines which contain viral protein antigens.

Thus, in one aspect, the invention is directed to a method to prepare a vaccine composition which method comprises providing a mixture of at least one viral protein antigen with a proteosome preparation in the presence of detergent and removing the detergent from the mixture by ultrafiltration. In preferred embodiments, the proteosome to viral antigen ratio in the mixture is greater than 1:1, preferably greater than 2:1, more preferably greater than 3:1 and more preferably greater than 4:1.

In other aspects, the invention is directed to vaccines prepared by the foregoing method, and in particular those vaccines where aggregates are formed between the viral antigen, preferably influenza hemagglutinin, and the proteosomes. Preferred size ranges are also described.

DETAILED DESCRIPTION OF THE INVENTION

Figure 1:
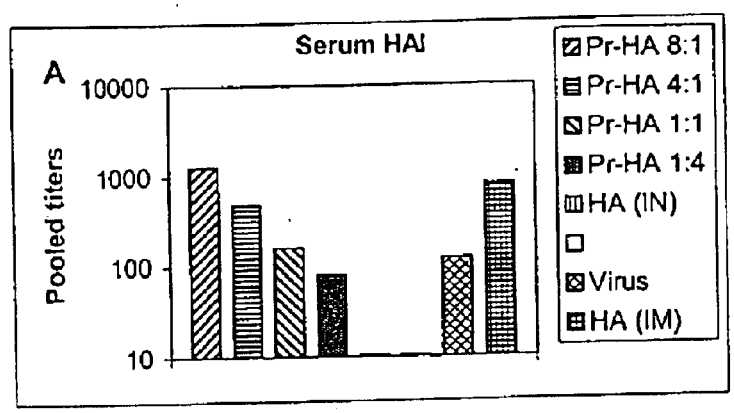
FIGS. 1A–C show serum immune responses induced by the invention vaccines.
Figure 1:
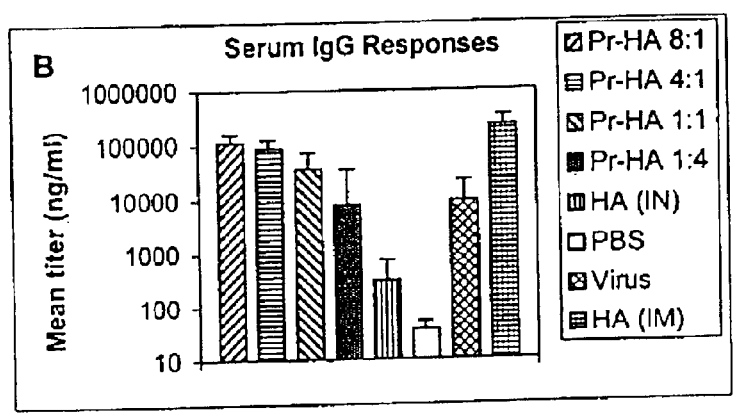
Figure 1:
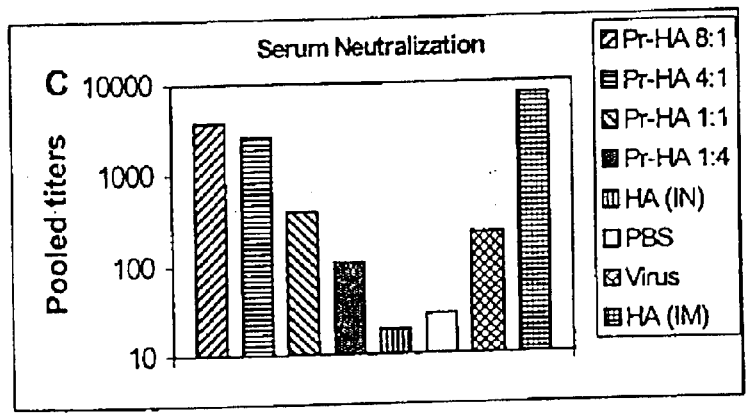

Peptide and lipopolysaccharide antigens from a diverse range of pathogenic organisms complexed to proteosomes have been demonstrated to induce enhanced mucosal and systemic immune responses following nasal or parenteral immunization in a variety of animal species. The invention herein describes improved compositions of, and improved processes for production of, proteosome-protein based vaccines as illustrated by vaccines designed to protect against influenza infection. The illustrated proteosome influenza vaccines, at equivalent doses of HA to those in injectable vaccines, induce comparable or enhanced serum virus specific immune responses, whereas the HA-influenza antigen without proteosomes induces significantly lower serum responses. Proteosome-influenza vaccines also generate high levels of specific mucosal nasal and lung IgA, whereas injected or nasal administration of influenza antigen alone induces trivial or very low levels of respiratory mucosal IgA. In addition, proteosome influenza vaccines convert immune responses to influenza antigens from a predominantly Type 2 response to a more balanced Type 1/Type 2 response or a predominant Type 1 response, whereas influenza antigens alone, given mucosally or by injection, elicit predominantly Type 2 responses. Type 1 responses promote the induction of cytotoxic T lymphocytes that are important for the resolution of influenza infections. In the past, Type 1 responses required live virulent or attenuated CAV nasal influenza vaccines. Prior reported ISIV administered either alone, or formulated with Biovector or virosome (with or without rLT), induce preferentially Type 2 immune responses.

In addition, proteosome nasal flu vaccines have been shown to be extremely well tolerated in mice and humans. No olfactory bulb or other central nervous system (CNS) involvement was seen in GLP mouse studies conducted with proteosome vaccines indicating that proteosome-flu vaccines are demonstrably inherently safer than the enterotoxin-based adjuvanted flu vaccines described above.

Finally, nasal proteosome influenza vaccine is immunogenic in humans and induces significant increases in serum HAI in healthy adults at a frequency and level not observed in subjects of this age group given CAV. At doses similar to those given by the injectable ISIV vaccines, the proteosome-influenza vaccine induces significant levels of secretory IgA in the nasal washes of humans. Thus, nasal proteosome-influenza vaccine has utility as an inactivated nasal influenza vaccine with immunogenic and safety properties superior to live CAV's and other nasally delivered or adjuvanted inactivated influenza vaccines.

The demonstration of the foregoing advantages of proteosome formulations with inactivated influenza antigens is typical of proteosomal compositions containing other antigen proteins and such compositions would be similarly effective in protecting against other respiratory or non-respiratory diseases using other viral or non-viral antigens.

The vaccines and compositions of the invention comprise two major components. The first component is a preparation of proteosomes. The second component is a protein antigen, preferably a viral antigen. Thus, bacterially derived antigens which are protein in nature can be used in the preferred formulations as well as viral antigens. The compositions are illustrated herein by use of a partially or fully purified preparation of influenza virus antigen. The antigen can be purified using detergent extractions and sucrose density gradient centrifugation to contain quantifiable amounts of influenza hemagglutinin (HA). Recombinant influenza proteins such as the hemagglutinin protein (HA) expressed in and purified from cell culture such as baculovirus or mammalian cell lines may also be used. The influenza component is generally referred to as influenza split-product or split-flu (for the antigen purified from natural sources) or recombinant HA (rHA).

By "proteosomal preparation" is meant an extract of outer membrane protein subjected to purification processes which result in the obtention of hydrophobic particles or vesicles as desired in, for example, U.S. Pat. No. 5,726,292, incorporated herein by reference, or in U.S. Pat. No. 4,707,543. Alternative and improved methods to prepare proteosomes are described in the examples below and illustrated with flowcharts. Any preparation method which results in the outer wall protein component in vesicular form is included within the definition of "proteosomal preparation."

The two components are formulated at specific initial ratios by the processes described so as to optimize interaction between the components resulting in non-covalent association of a significant portion of the two components to each other. The processes generally involve the mixing of the components in a selected solution of detergent(s) and then removing the detergent(s) by diafiltration/ultrafiltration methodologies using flow and membrane parameters optimized for the vaccines of the invention.

One feature of the present invention is that the ratio of proteosomes to antigen contained in the composition is preferably greater than 1:1, more preferably greater than 3:1, more preferably greater than 4:1. The ratio can be as high as 8:1 or higher. The detergent-based solutions of the two components may contain the same detergent or different detergents and more than one detergent may be present in the mixture subjected to ultrafiltration/diafiltration. Suitable detergents include Triton, Empigen, and Mega-10. Other detergents can also be used. The detergents serve to solubilize the components used to prepare the composition. The use of a mixture of detergents may be particularly advantageous. This mixture is, of course, removed by diafiltration/ultrafiltration prior to final formulation.

Another feature of the process for preparing the compositions of the invention which may then be formulated into vaccines is that the resultant composition is such that it can be filtered through a $0.8\mu$ filter, a $0.45\mu$ filter or a $0.2\mu$ filter. This permits sterilization to be performed by filtration, obviating the necessity of adding an antiseptic such as thimerasol. This is highly advantageous as it is desirable to eliminate any complications by virtue of the presence of such contaminants.

The compositions prepared by the method of the invention are ultimately formulated into vaccines by, if desired, filtration as described above, addition of diluents and carriers, buffers, and the like.

As will be illustrated below, vaccines wherein HA is the antigen, or indeed vaccines containing any protein antigen, can be made as multivalent vaccines. This can be accomplished in two ways. The initial mixture prior to diafiltration/ultrafiltration may contain a mixture of the desired antigens provided initially as separate components optionally in the presence of different detergents or in the presence of the same detergent; the mixture of antigens is then mixed with the detergent-0containing proteosome preparation and processed as described above. Alternatively, the composition obtained after diafiltration from a single (or multiple) antigens can be mixed with similarly prepared preparations from one or more additional antigens. Thus, illustrated below is a trivalent vaccine composed of three different HA antigens.

In addition to the features of the process for preparing the composition to be formulated into vaccines, the proteosomal composition itself may be prepared by an improved process. Thus, the multiplicity of steps set forth in the prior art may be short circuited, or additional steps or substituted steps may be employed. In one important embodiment, the preparation process involves one or more precipitations in the presence of ethanol as described in the examples below, followed by re-extracting of the proteosomes in 0.1 –1% detergent solutions, typically using Empigen, thus resulting in a more uniform product. In addition, the ammonium sulfate precipitation steps described on the prior art processes may be eliminated, whether or not the ethanol precipitation steps are employed.

Thus, the compositions prepared by the method of the invention can be formulated into vaccines that can be delivered by a mucosal (such as nasal, oral, oropharyngeal, or rectal) or parenteral (such as intramuscular or subcutaneous) or transdermal route to induce both serum and mucosal antibodies and immune responses.

As shown below, nasal vaccine delivered by liquid or spray to mice induces specific anti-influenza immune responses including serum IgG antibodies and hemagglutination inhibition (HAI) antibodies. HAI responses are significant since their induction is known to correlate with protection against influenza in humans. The vaccines also result in mucosal antibodies including IgA in mucosal secretions collected from the nasal cavity or lungs and in switching of predominant Type 2 type responses to balanced or predominant Type 1 responses as measured by IgG1/IgG2a ratios and induction of Th1 cytokines such as interferon gamma without Th2 cytokines such as IL-5. Such responses are predictive of other cellular mediated responses such as development of cytotoxic T cells (CTLs). The ability of a nasal vaccine of the instant invention to elicit these three types of responses indicates that the vaccine can provide a more complete immunity since functional serum antibodies (including HAI antibodies), functional nasopharyngeal and lung IgA antibodies that can neutralize influenza virus and Th1 responses that help provide elimination of residual or intracellular virus are all important mediators of protection against influenza virus infection. This is consistent with the results showing that the vaccines described protect mice against weight loss and death associated with challenge of mice with virulent influenza virus.

In addition to administration by mucosal routes, such as nasal administration, the vaccines of the invention can also be administered parenterally, for example, by injection (e.g. intramuscularly or s.c.). Intramuscular injection is demonstrated below to provide higher levels of serum antibodies than provided by administering split-flu vaccine without proteosomes.

As shown below, administration of the vaccines of the invention by the nasal route to mice even using a greater number of immunizations (three) than typical for clinical applications (one or two immunizations) and using doses up to twenty fold, the highest expected human dose was well-tolerated. Importantly there was no evidence of inflammation in the olfactory bulb region of the CNS unlike other enteroxigenic mucosal adjuvants described above.

As further shown below, in humans, the invention vaccine prepared with split influenza antigen given by nasal spray was well tolerated without any serious adverse effects. At optimal doses the vaccine induced serum HAI responses in more than 50% of volunteers (even in volunteers profoundly seronegative to the influenza strain tested), the majority with titers equivalent or exceeding those that correlate with protection against disease caused by influenza virus. The serum HAI titers were significantly higher than those induced by split antigen alone given intranasally, which induced an HAI response in less than 13% of volunteers. The vaccine also induced nasal wash secretory IgA at levels in significantly more volunteers than, and significantly higher than, that produced following immunization with split vaccine alone given nasally or by injection. The doses of proteosome-flu vaccines that induced mucosal and systemic immune responses in humans (7.5–30 $\mu$g) were similar to those of the current injectable vaccines (15 $\mu$g) and would not have been predicted. In previous human studies, using proteosome shigella vaccines, to obtain optimal serum and mucosal immune responses following nasal immunization in humans, it was necessary to give the proteosome-shigella vaccines at doses of shigella antigen of 1,000 $\mu$g to 1,500 $\mu$g (fifty to 100 (50–100) fold higher than the average doses of influenza hemagglutinin antigen used for the proteosome-flu vaccines prepared by the methods of the present invention.

As set forth above, the invention includes monovalent and multi-valent (including, bi- or tri-valent) vaccines. The multivalent preparation can be obtained by combining individual monovalent proteosome-flu vaccines, or monovalent influenza antigens can be combined together to form a multivalent antigen mixture, then complexed with proteosomes to produce the composition to be formulated as a multi-component proteosome-flu vaccine.

For parenteral, nasal, oral or suppository use, the vaccine may contain the active ingredients plus potentially large amounts of a variety of excipients or adjuvants including oils, emulsions, nano-emulsions, fats, waxes, buffers, or sugars, as diluents or vehicles customary in the art to provide stable delivery of the product in the desired delivery format.

As is well-known in the art, a variety of protocols for administering the vaccines of the invention can be employed. The vaccines may be used in an individual protocol comprising several administrations of the vaccines of the invention, or the invention vaccines can be used in combination protocols with other formulations. The selection of antigens is governed by the nature of the infective agent; the design of a particular protocol for administration, including dosage levels and timing of dosing are determined by optimizing such procedures using routine methods well known to the skilled artisan.

While illustrated for influenza vaccination, vaccines similar to those exemplified but containing other antigens are successful in protecting humans or animals (as in veterinary applications) against viral or microbial diseases or against certain toxins or biologic threat agents or allergies acquired by mucosal routes, i.e., by inhalation, and also by ingestion or sexual transmission. The invention includes preventive or therapeutic vaccines delivered by mucosal or parenteral routes using cell surface or internal protein antigens for vaccines against microbial diseases, allergies or cancer.

The compositions resulting from the process of the invention are clearly different from the technologies known in the art. For instance, unlike live attenuated cold-adapted vaccines (CAV), the vaccines described herein contain non-living antigens which are purified or recombinant components. The compositions are clearly different from MF59 emulsions, liposome, virosome, monophosphoryl lipid A (MPLA) or Biovector technologies since proteosomes are essentially composed of bacterial outer membrane proteins and contain only trivial or minor amounts of native bacterial lipids, whereas MF59 lipid emulsions, liposomes or virosomes consist of many lipids while MPLA and Biovector technologies are lipid-saccharide entities with small (MPLA) or larger (Biovector) amounts of saccharides. None of these adjuvants contain substantial amounts of proteins (bacterial or otherwise).

A comparison of the nature and properties of the vaccines of the present invention with those described by Dalseg, R., et al., *Vaccines* (1998) 96:177–182, cited above, demonstrates the advantages of the present invention. The Dalseg compositions suffer from drawbacks set forth above with respect to attenuated virus; the antigenic component in the Dalseg vaccines is formalin-inactivated whole influenza virus, as opposed to the purified proteins used in the vaccines of the present invention. Vesicles obtained as an extracted outer membrane preparation from *Neisseria meningitides* by an unspecified method were mixed with formalin-inactivated influenza virus and either sonicated or simply mixed. As no diafiltration or ultrafiltration process is applied to the mixture, detergent present in the composition comprising the vesicles remains in the composition. The compositions thus prepared by Dalseg provide inferior results to those of the vaccines of the present invention; four doses of the Dalseg compositions were required in order to observe the results and the vaccine was not shown to be protective.

Prior reported compositions utilizing proteosomes as outlined in the review article by Lowell cited above, employed ratios of proteosomes to antigens of 1:1 or less; ratios as low as 1:20 were used. Prior art vaccines therein described showed optimal responses required that optimal responses required antigen doses of up to 1,000 $\mu$g or 15,000 $\mu$g whereas vaccines of the invention are effective in humans using antigen doses in the 7.5–30 $\mu$g range.

As to the process for preparation per se, it has been shown that it is possible to use a 100,000 molecular weight cutoff in the diafiltration/ultrafiltration procedure thus resulting in enhanced efficiency; similarly more efficient is the possibility to subject several antigens simultaneously in the presence of proteosomes to a one-step diafiltration/ultrafiltration procedure.

The following examples are intended to illustrate but not to limit the invention.

EXAMPLE 1

Production of Proteosomes

Outer membrane protein proteosome preparations were purified from Group B type 2 *Neisseria meningitides* by extraction of phenol-killed bacterial paste with a solution of 6% Empigen BB (EBB) (Albright and Wilson, Whithaven, UK) in 1 M calcium chloride followed by precipitation with ethanol, solubilization in 1% EBB-Tris/EDTA-saline and then precipitation with ammonium sulfate. The precipitates were re-solubilized in the 1% EBB buffer, dialyzed and stored in 0.1% EBB at −70° C. A flow chart of the process (Flowchart 1) is shown on the following pages. Proteosomes may also be prepared by omitting the ammonium sulfate precipitation step to shorten the process (Flowchart 1A). An alternative process that is also successful is shown in Flowchart 1B.

EXAMPLE 2

Preparation of Influenza Antigen (Influenza HA or Flu-HA) Containing Quantified Amounts of Influenza Hemagglutinin (HA)

Split Antigen

Preparation was performed as outlined in Flowchart 2. Briefly, preparation involved harvesting allantoic fluid from virus inoculated eggs followed by clarification, inactivation of the virus, concentration by diafiltration/ultrafiltration, banding the virus on sucrose gradient density centrifugation, pelleting, extracting the re-suspended pellet with Triton X-100, or NP-40 or other suitable detergent, and centrifuging and collecting the supernatant. This process was repeated as required, analyzed as described in Flowchart 2, pooled and stored at 2–8 degrees C.

Recombinant Baculovirus Expressed Influenza HA

Briefly, Influenza HA (A/Texas/36/91) was expressed and purified by conventional techniques as described in (Ref Gail Smith, et. al.). The resultant protein was >95% HA as determined by PAGE reducing gels. HA was quantified in the final complex using densitometry and comparing the intensity of the recombinant HA bands in the complex with the intensity of the bands of known concentrations of the recombinant protein.

EXAMPLE 3

Preparation of Proteosome-influenza HA Vaccine

Portions of stock influenza split product antigens were complexed to and formulated with proteosomes using diafiltration/ultrafiltration methods described in Flowchart 3 or by using dialysis. For either method, the influenza split product was dissolved in saline buffered solution containing the desired detergent e.g. Empigen BB (EBB) at 1% or, at 0.1%–2% of EBB or other suitable detergent depending on the type of detergent used and was then mixed with proteosomes in the saline buffered 1% Empigen solution (or other appropriate detergent at appropriate concentrations as described above) at various proteosome:HA (wt/wt) ratios ranging from 4:1 to 8:1 including 1:4, 1:1, 2:1, 4:1 and 8:1. To remove Empigen, the mixture was then subjected to ultrafiltration/diafiltration technology as described in the Flowchart 3 or was exhaustively dialyzed across a dialysis membrane with a 10,000 Molecular Weight cut-off (MWCO) or functionally similar membranes with MWCO ranges of 1,000–30,000 against buffered saline for 1–2 weeks at 4° C. exchanging at least 500 parts buffer each day.

At various steps, single radial immunodiffusion (SRID) was used to measure potency. The halo immunodiffusion technique was used to accurately determine the content of formulate split-flu antigen with proteosomes at various ratios. This methodology is the classical potency assay for split-flu products based on hemagglutinin content for the final vialed materials. Reagents were obtained from National Institute for Biological Standards and Control (NIBSC), Hertfordshire, United Kingdom. Reference: Hudson, L. and Hay, F. C., *Practical Immunology*, ed. Blackwell Scientific Publication: Third Edition; pages 230–233.

Multivalent vaccines may be prepared by making individual monovalent proteosome vaccines and then combining them at the required proportions prior to final formulation and fill. Multivalent preparations may also be formulated by pooling individual antigens in the desired proportions and formulating the mixture with proteosomes as outlined in Flowchart 3. Vaccines were passed through membrane filters of 0.8 $\mu$m pore size and stored at 4° C. prior to and during the immunizations.

Manufacture of Proteosome Bulk Material:
FLOWCHART 1

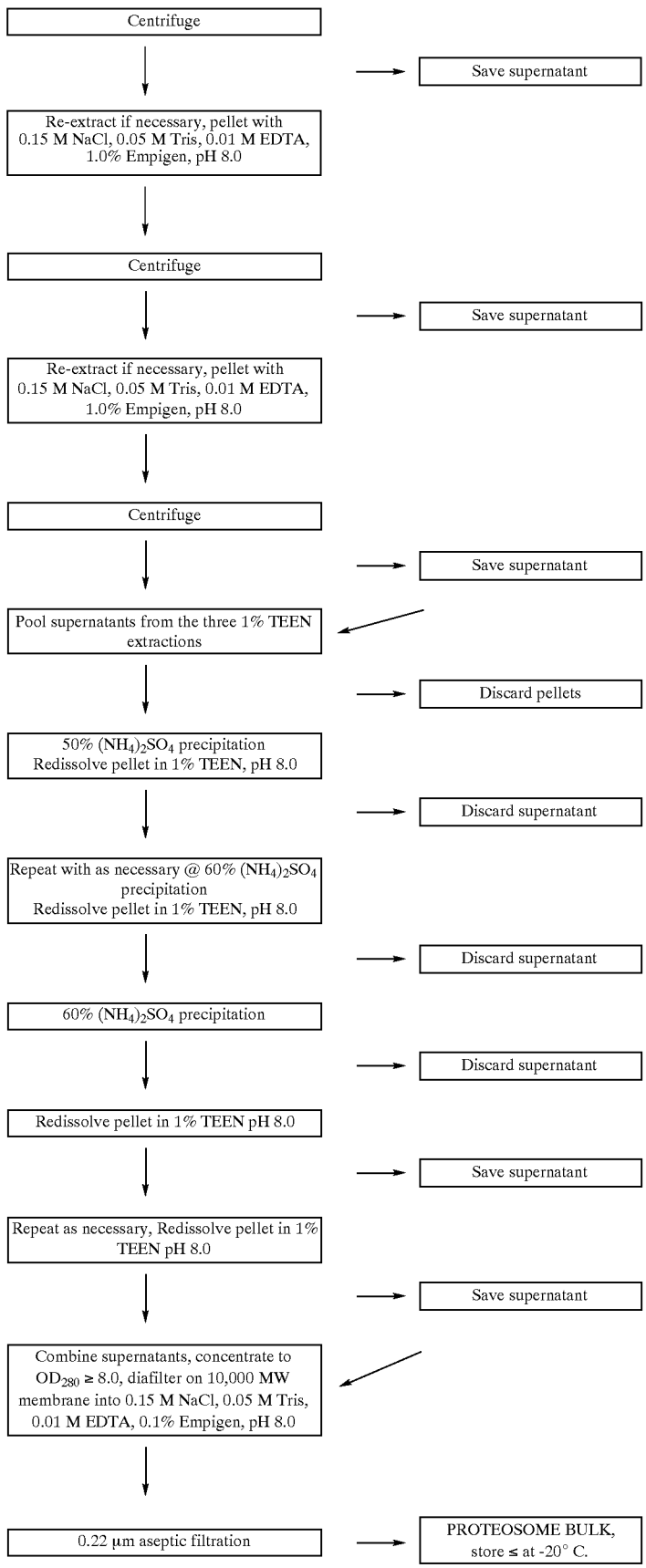

-continued
Manufacture of Proteosome Bulk Material:
FLOWCHART 1A
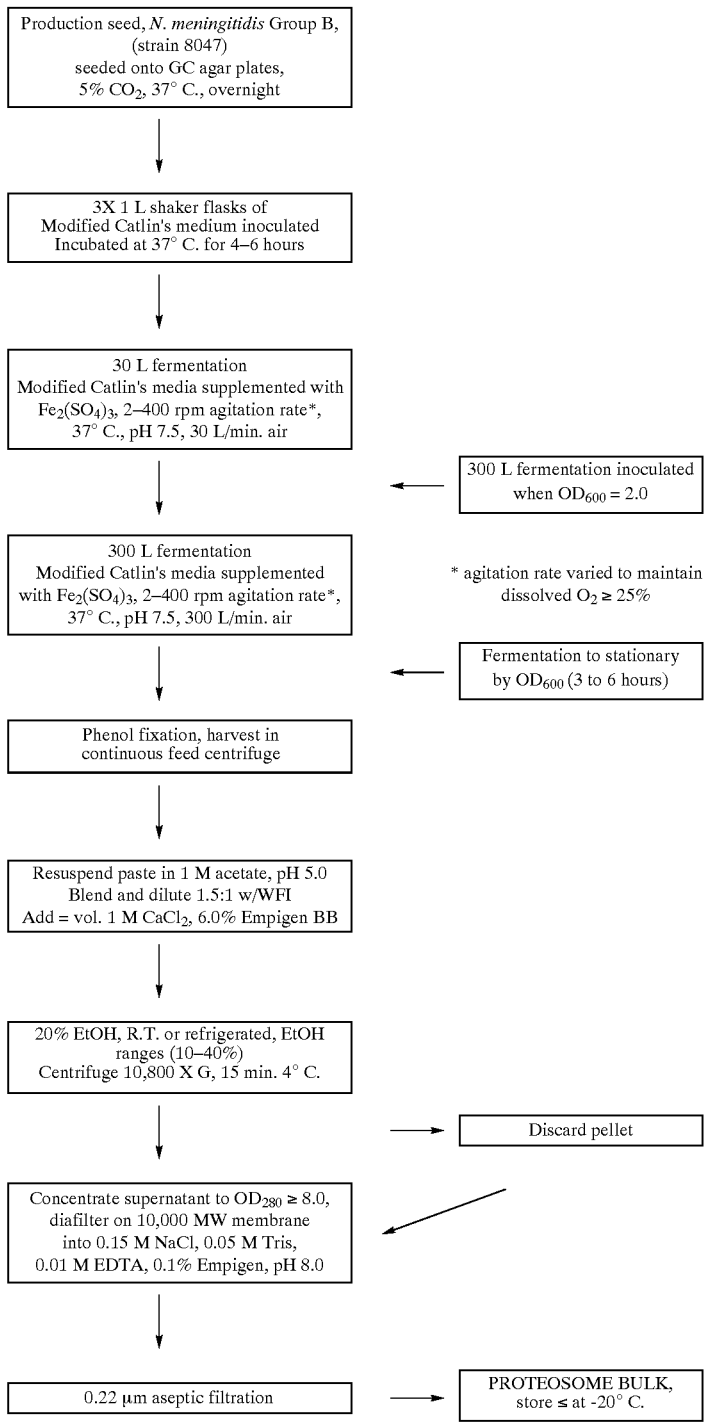
Manufacture or Proteosome Bulk Material
FLOWCHART 1B

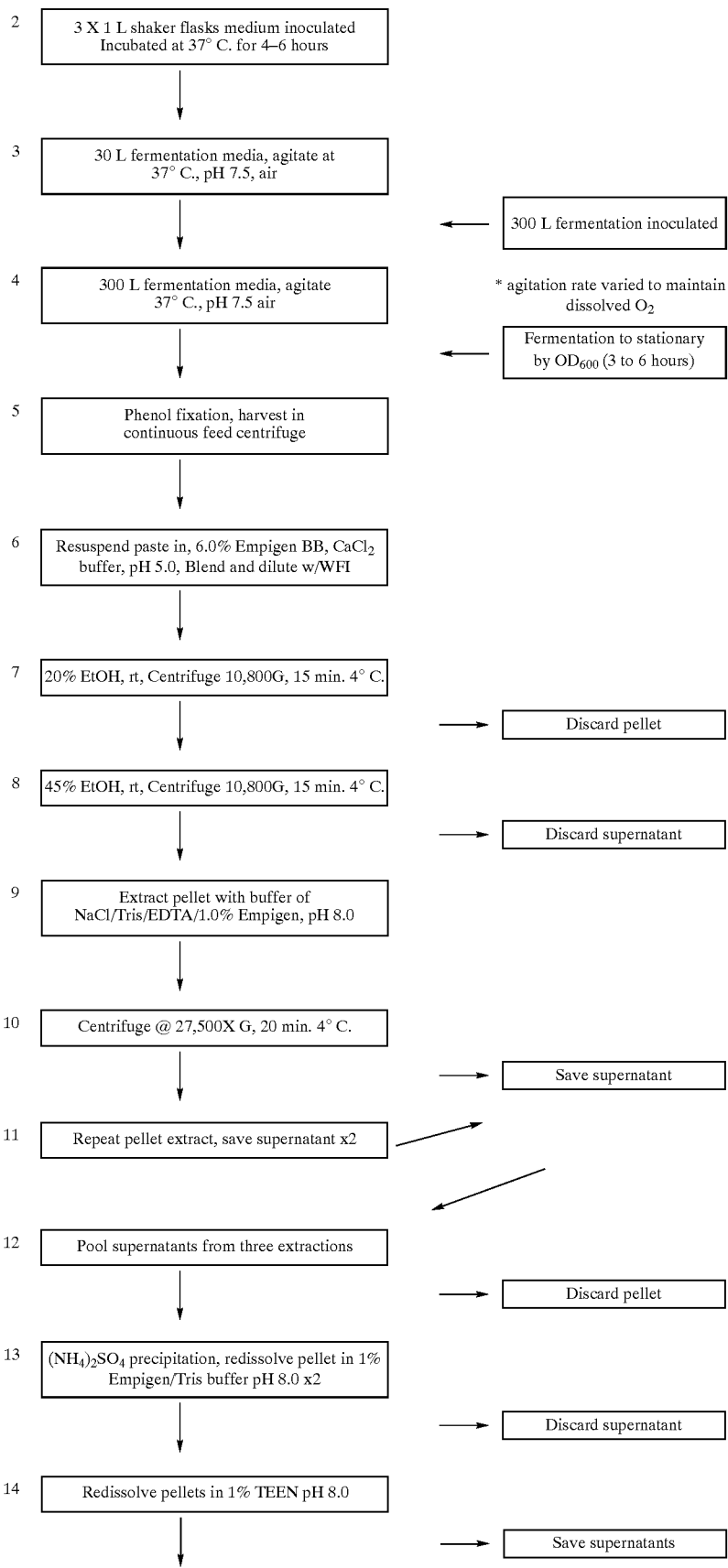

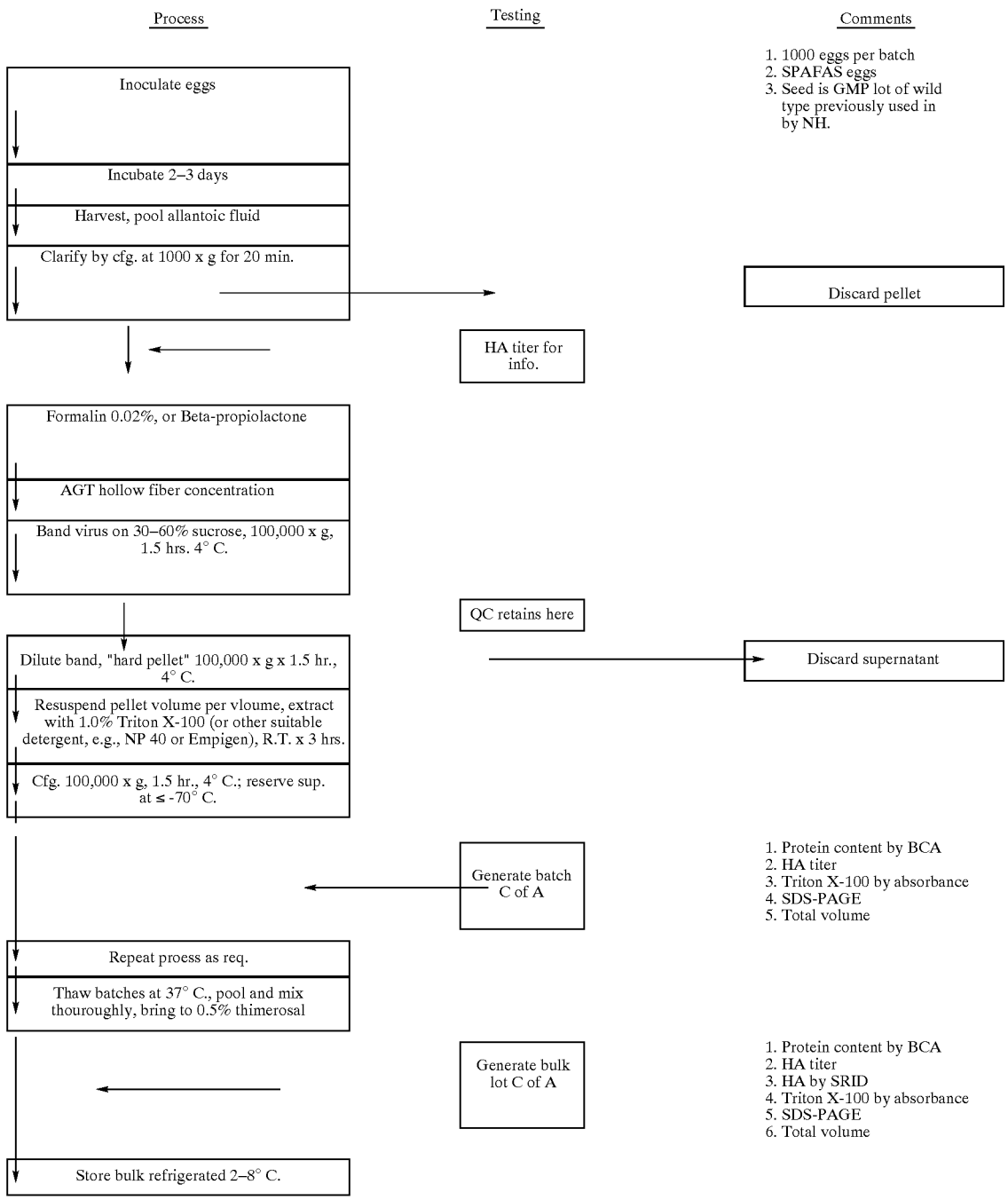

-continued
Proteosome-Influenza Vaccine (Monovalent-Trivalent)
Process by Diafiltration/ultrafiltration:
FLOWCHART 3

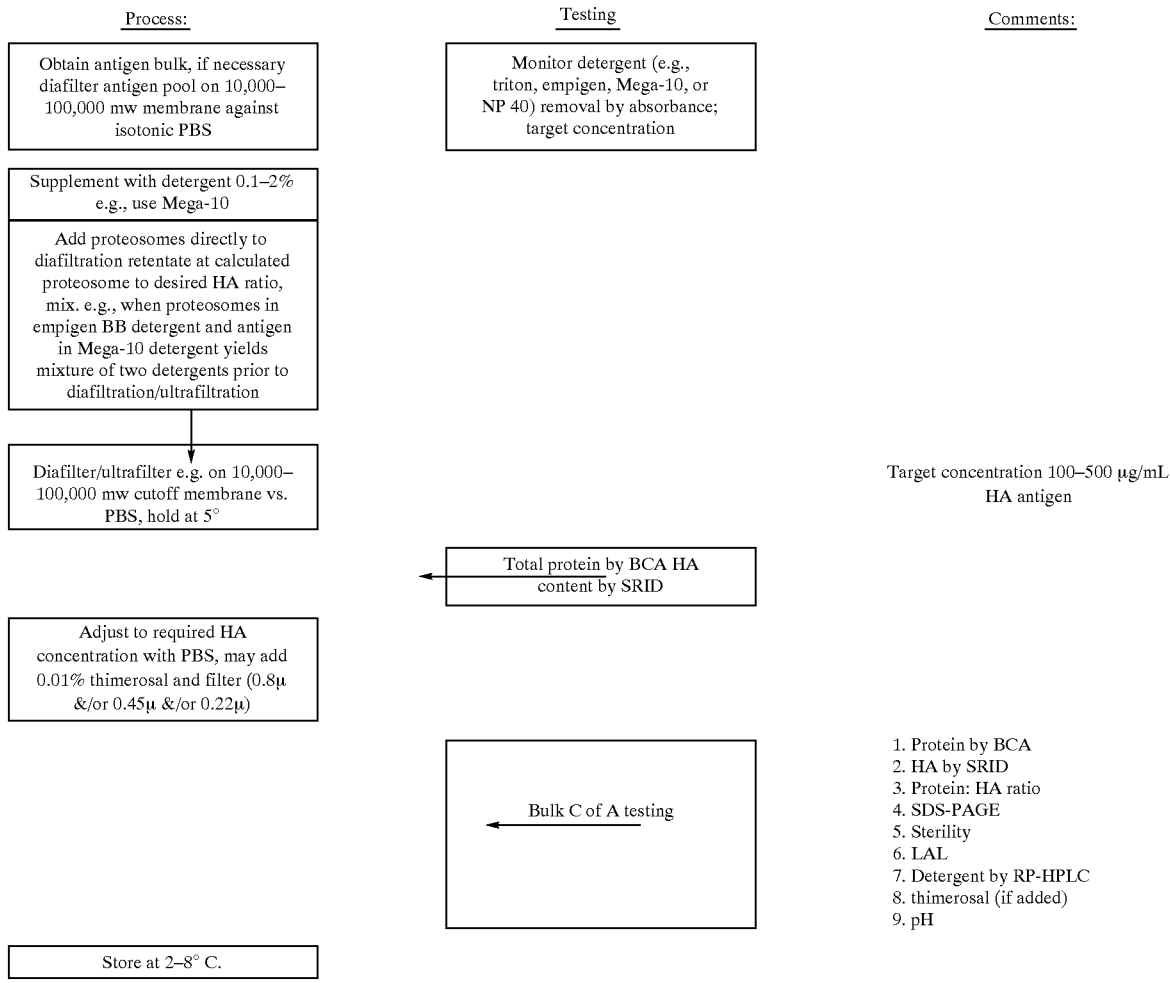

EXAMPLE 4

This Example Describes the Mouse Immunization Protocols Used

One day prior to the first immunization randomly selected mice were pre-bled. BALB/c mice were immunized intranasally or intramuscularly on days 1 and 21 with antigens in volumes of 25 or 100 µl respectively containing between 0.3 and 10 µg HA A/Taiwan/1/86 or A/Beijing/262/95 as split influenza antigen or A/Texas/36/91 as baculovirus recombinants, alone or formulated with proteosomes (proteosome-flu vaccine or proteosome-rHA) at proteosome:HA ratio's at complex initiation of 1:4, 1:1, 2:1, 4:1 and 8:1 wt/wt. In some examples control mice were given a single intranasal immunization with either phosphate buffered saline or 0.04 $LD_{50}$ mouse-adapted live influenza A/Taiwan/12/86 on day 1. Animals were bled on days 20 and 35 via the orbital sinus vein or by cardiac puncture. Nasal and lung lavage samples were taken on day 35. The lungs of each mouse were surgically exposed and a canula inserted in the trachea. Using a syringe containing phosphate buffered saline supplemented with 0.1% bovine serum albumin and protease inhibitors (0.2 mM AEBSF, 1 µg/ml Aprotinin, 3.25 µM Bestatin and 10 µM Leupeptin), 1 nasal lavage sample (approximately 1 ml) and 2 lung lavage samples (2×1 ml) were collected. The lung lavage fluids were combined and lavage fluids from individual animals vortexed and centrifuged to remove cell debris and supernatants stored at −70° C. until assayed by ELISA.

EXAMPLE 5

This Example Describes the Serum Hemagglutination Inhibition Assay (HAI)

Prior to determination of HAI activity, mouse or human sera were heated at 56° C. to inactivate complement. Elimination of non-specific agglutination was achieved by treating mouse sera with receptor destroying enzyme (RDE). To 0.1 ml of serum was added 0.4 ml of RDE (100 units/ml) for 12 to 18 hr at 37° C. Three hundred ml of sodium citrate (2.5%) was added for 30 min at 56° C. to inactivate the RDE. The sample volume was made up to 1 ml with PBS (to give final sample dilution of 1:10). Two-fold serial dilutions of each sample were tested for their ability to inhibit the agglutination of 0.5% chick red blood cells by A/Taiwan/1/86 virus in a standard HAI assay.

EXAMPLE 6

This Example Describes the Serum ELISA Assay to Measure Specific Anti Flu Antibodies in Sera, in Lung and Nasal Cavity Fluids Sera were collected after each immunization; lung and nasal cavity lavage fluids were collected after the last immunization. Nasal wash and lung lavage starting dilutions were 1 in 4 and serum starting dilutions were 1/100. ELISA was performed using whole virus as the detecting antigen. Briefly, 96 well round bottom microtiter plates (Immulon 2, Dynatech, Chantilly, Va.) were coated with antigen and incubated overnight. After aspiration of the antigen using a plate washer, plates were washed once with PBS containing Tween (PBS-T) and incubated with blocking solution containing PBS-T plus plus 2% powdered milk. After aspirating the blocking solution and washing with PBS-T, samples of sera, lung or nasal cavity lavage fluids, serially diluted 2-fold in blocking solution, were added and the plates were incubated for two hours at 37° C. After washing with PBS-T, affinity purified horseradish peroxidase (HRP)-labeled goat anti-mouse IgG or IgA was added and plates were incubated at 37° C. for 30 min. After aspirating and washing twice with PBS-T, developing solution was added and plates were incubated for 15 min at r.t. prior to determining the absorbance values using a microtiter ELISA plate reader (Molecular Devices, Menlo Park, Calif.). Absorbances in the ELISA plate reader were determined at specified times. Antibody titers in the Figures are expressed as ng/ml of specific IgG or IgA determined from a standard curve produced using an ELISA capture assay using affinity purified mouse IgG and IgA standards (Sigma).

EXAMPLE 7

This Example Describes the in Vitro Neutralization Assay to Measure Influenza Virus Neutralizing Antibodies in Serum and Lung Lavage Fluids Neutralization of virus infectivity was determined by direct observation of cell lysis and cytopathic effect (CPE) in MDCK cells. The assay was performed in 96-well plates. Each sample was run in octuplicate. Serial dilutions of test samples (sera or lung lavage fluids) were incubated with 100 $TCID_{50}$ of live influenza virus homologous to the vaccine strain, incubated for 90 minutes at room temperature and added to $2.4 \times 10^5$ MDCK cells/well. Plates were incubated at 32° C./5%$CO_2$ for the remainder of the assay. Viral neutralization was determined during the virus growth phase (5–7 days of incubation) by evaluation of CPE using an inverted microscope. Neutralizing titers were determined by the Kärber formula ($TCID_{50}=\Delta-\delta(S-0.5)$) where "$\Delta$" is the $\log_{10}$ of the dilution with 100% positive cultures, "$\delta$" is the $\log_{10}$ of the dilution factor and "S" is the sum of positive cultures per dilution including those at dilution with 100% infected cultures.

EXAMPLE 8

Figure 2:
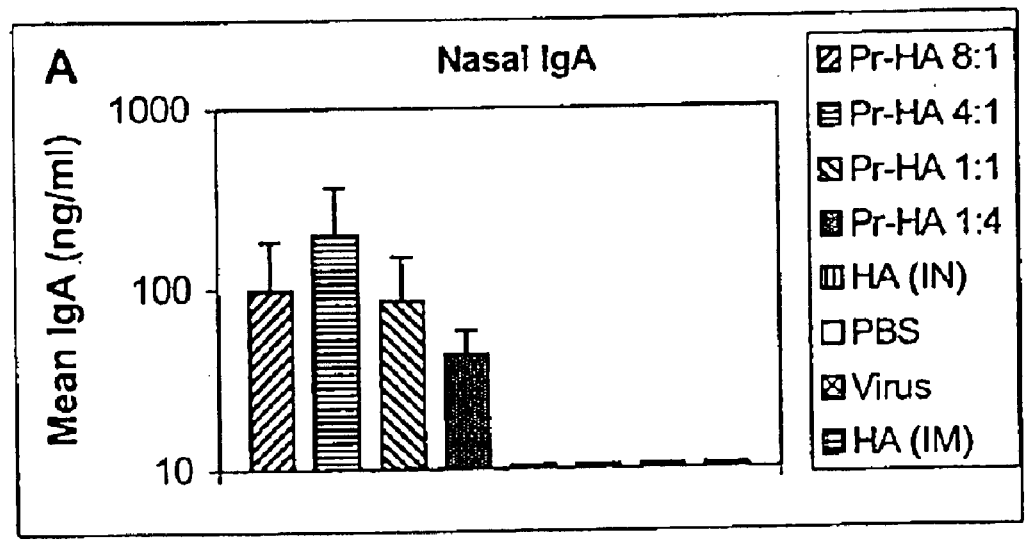
FIG. 2 shows mucosal immune responses induced by these vaccines.
Figure 2:
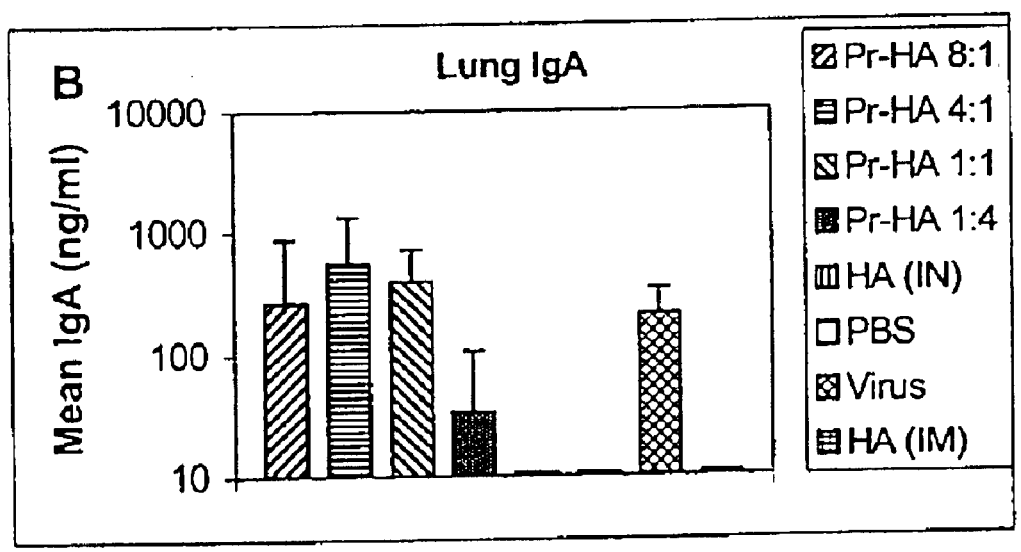

Evidence of Enhanced Immunogenicity and Immunity as Measured by Enhanced Serum HAI and Virus Specific IgG Titers Elicited by Proteosome-HA Vaccines This example shows the serum and mucosal antibody responses induced by proteosome-flu vaccines following nasal immunization with monovalent vaccines prepared with A/Taiwan/91 influenza split antigen (FIGS. 1 and 2) or purified baculovirus recombinant HA (A/Texas/36/91) (Table 1) by the dialysis method. Similar results were obtained using proteosome-flu vaccines prepared by the scalable diafiltration method (See Example 12 below).

Anti-influenza IgG antibodies in sera where analyzed by HAI; IgG in sera and IgA antibodies in lung and nasal cavity fluids were analyzed by ELISA; and IgG in serum and IgA and IgG in lung lavage fluids were tested for virus neutralizing activity. The responses were compared to the collections of samples from saline immunized animals and from animals immunized with influenza split product delivered alone without proteosomes or with animals immunized with control vaccines containing proteosomes and an irrelevant antigen (HBsAg). Results are shown and summarized in FIGS. 1–2 and Table 1. Briefly: nasal proteosome-flu and proteosome-rHA vaccines at the optimum ratio of proteosomes to HA. The optimal immune responses were obtained for proteosome:HA formulation ratio's between 4:1 and 8:1.

1. elicited 6–32-fold higher serum HAI responses than Split Flu alone given nasally and titers that are equivalent to HAI titers elicited by giving the split product HA vaccine alone by injection (FIG. 1A and Table 1),
2. elicited up to 250-fold higher Serum IgG responses than Split Flu alone given nasally and elicits responses comparable to nasal live virus or equivalent or up to 5-fold greater than split flu given by injection (i.m.) (FIG. 1B. and Table 1),
3. induced serum neutralization titers equivalent to injectable split influenza vaccine and >100-fold greater than split flu antigen alone by the nasal route (FIG. 1C),
4. elicited >1,000-fold higher IgA responses in the nasal cavity than Split Flu alone given nasally or by injection (i.m.) (FIG. 2A),
5. elicited 20–1000-fold higher specific IgA responses in the lung than Split Flu alone given nasally or by injection (i.m.) (FIG. 2B and Table 1),
6. elicited responses equal to or better than live virus (FIGS. 1–2),
7. elicited neutralizing antibodies in the lung fluid secretions. Following nasal immunization only the 4:1 proteosome-flu vaccine induced functional antibodies in lung lavage fluids capable of completely inhibiting the cytopathic effect of the virus in 8/8 replicates at <1 in 2 dilution. No in vitro neutralization was observed for lung lavage fluids from mice immunized with the Flu antigen alone either after nasal or intramuscular immunization, and
8. induced enhanced serum IgG and equivalent serum HAI titers compared to split antigen alone after parenteral immunization (Table 2).

Table 1. Serum IgG and mucosal IgA induced by nasal proteosomes-rHA vaccine (10 μg HA per dose @4:1 Pr:HA ratio) in mice

TABLE 1

Serum IgG and Mucosal IgA induced by nasal proteosome-rHA vaccine (10 μg HA per dose @ 4:1 Pr:HA ratio) in mice

| | Pr-rHA nasal | rHA nasal | rHA IM | PBS |
|---|---|---|---|---|
| Serum IgG (ng/mL)* | 188,956 | 6,006 | 43,885 | 50 |
| HAI (GMT)** | 160 | 20 | 40 | 10 |
| Lung IgA (ng/mL)*** | 500 | 20 | 20 | 20 |

All samples taken 14 days post 2nd immunization.
* and *** are Geometric Means for 5 mice/group;
**HAI for sera pooled from 5 mice/group Table 2. Serum IgG and HAI responses Induced by intramuscular proteosome Split flu vaccine (3 μg HA per dose @4:1 Pr:HA ratio) in mice

TABLE 2

Serum IgG and HAI responses Induced by intramuscular proteosome Split flu vaccine (3 μg HA per dose @ 4:1 Pr:HA ratio) in mice

|  | Pr-HA 4:1 | Pr-HA 1:1 | Pr-HA 1:4 | HA |
|---|---|---|---|---|
| Serum IgG (ng/mL)* | 373,400*** | 189,600 | 155,400 | 81,110 |
| HAI (GMT)** | 320 | 320 | 320 | 320 |

All samples taken 14 days post 2$^{nd}$ immunization.
* and *** are Geometric Means for 8 mice/group;
**HAI for sera pooled from 8 mice/group;
***p = <0.01 compared with HA alone

EXAMPLE 9

Figure 3:
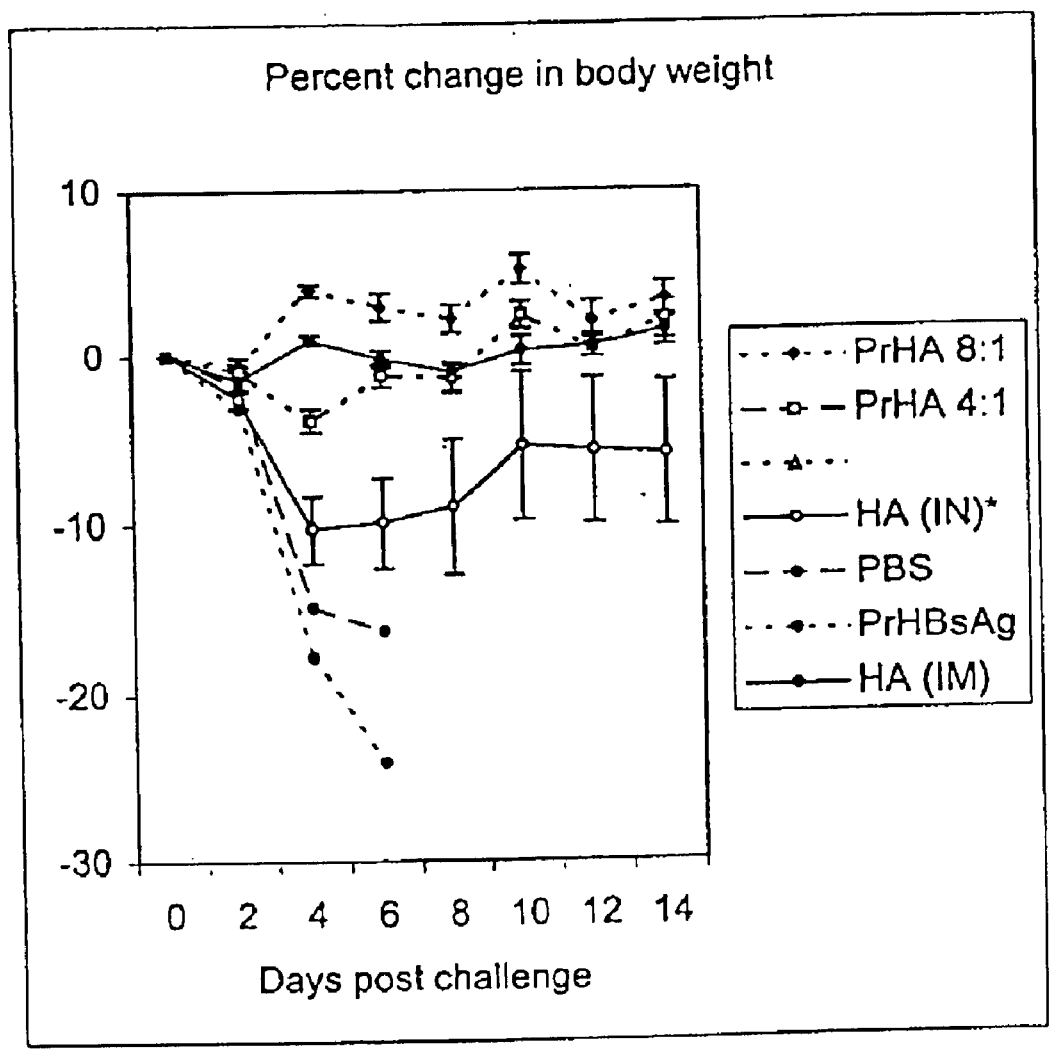
FIG. 3 is a graph showing protection of mice immunized with the recombinant form of the invention vaccine.

This Example Describes the Mouse Immunization Live Virus Challenge Protocols and Results To demonstrate vaccine-induced protection against live virus challenge, groups of vaccine immunized and control animals (treated as described in example 4 above with nasal proteosome-flu (A/Taiwan/12/86) vaccine) were challenged on day 36 with specific 4 LD$_{50}$ of live mouse-adapted influenza. Mouse protection was assessed by monitoring weight changes in the animals over 14 days following challenge. Mice that lost 30% or more of their starting weight and that showed severe signs of clinical morbidity were sacrificed. Data showing protection elicited by the proteosome flu vaccine are shown and summarized in FIG. 3.

Briefly, complete protection against significant or lethal weight loss from challenge with virulent homologous virus is shown for the nasal proteosome-flu vaccines prepared at Pr:HA ratio's of between 4:1 and 8:1 whereas the HA without proteosomes showed a significant weight loss during the experiment. Furthermore, the protection induced is equal to that induced by the split flu vaccine alone given by injection. Protection that may be obtained for vaccines formulated at lower Pr:HA ratio's (such as 1:1) even though such formulations induce sub-optimal serum and mucosal immune responses may be due to the inability of the animal protection model to differentiate effectively between formulations prepared at sub-optimal initial formulation ratios.

EXAMPLE 10

This Example Describes the Shift of Immune Responses from Type 2 to Type 1 by Nasal Proteosome Influenza Vaccines The IgG1/IgG2a ratio in mouse serum is a surrogate marker for the type of T cell response induced by a vaccine. Th1(IgG1/IgG2a ratio's <1) correlates with the induction of strong cell mediated immune responses (in addition to serum antibodies); while Th2 (IgG1/IgG2a ratio's >1) predict the induction of strong humoral responses. Levels of murine IgG sub-types, IgG1 and IgG2a were determined in the sera using ELISA assay kits (SBA Clonotyping System/HRP, Southern Biotech Assoc.) following nasal or intramuscular immunization with the proteosome-flu vaccines or flu antigen alone using either monovalent split influenza vaccine or recombinant baculovirus derived HA.

Figure 4:
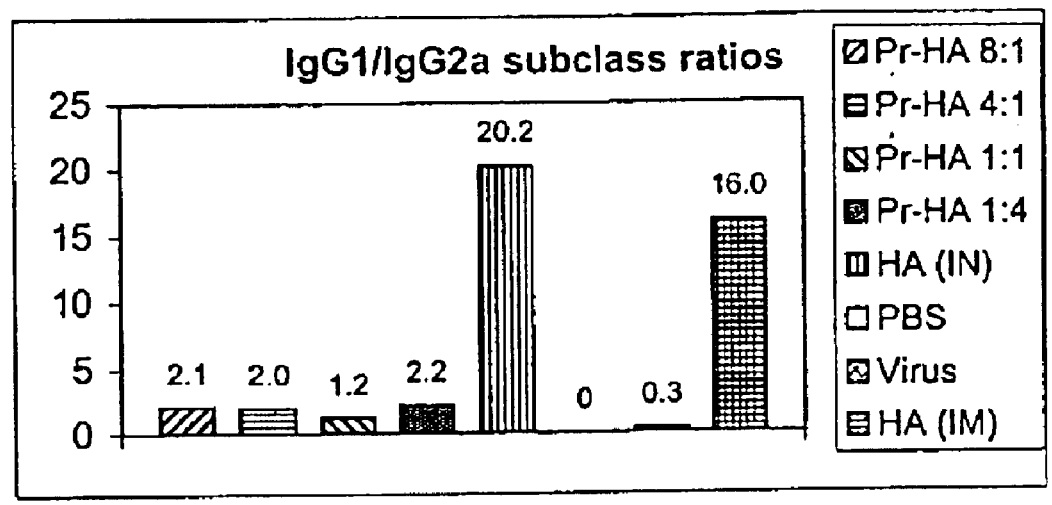
FIG. 4 is a graph showing the shift of immune response induced by split antigen vaccine from a Type 2 response to a balanced Type 1/Type 2 response in mice.
Figure 5:
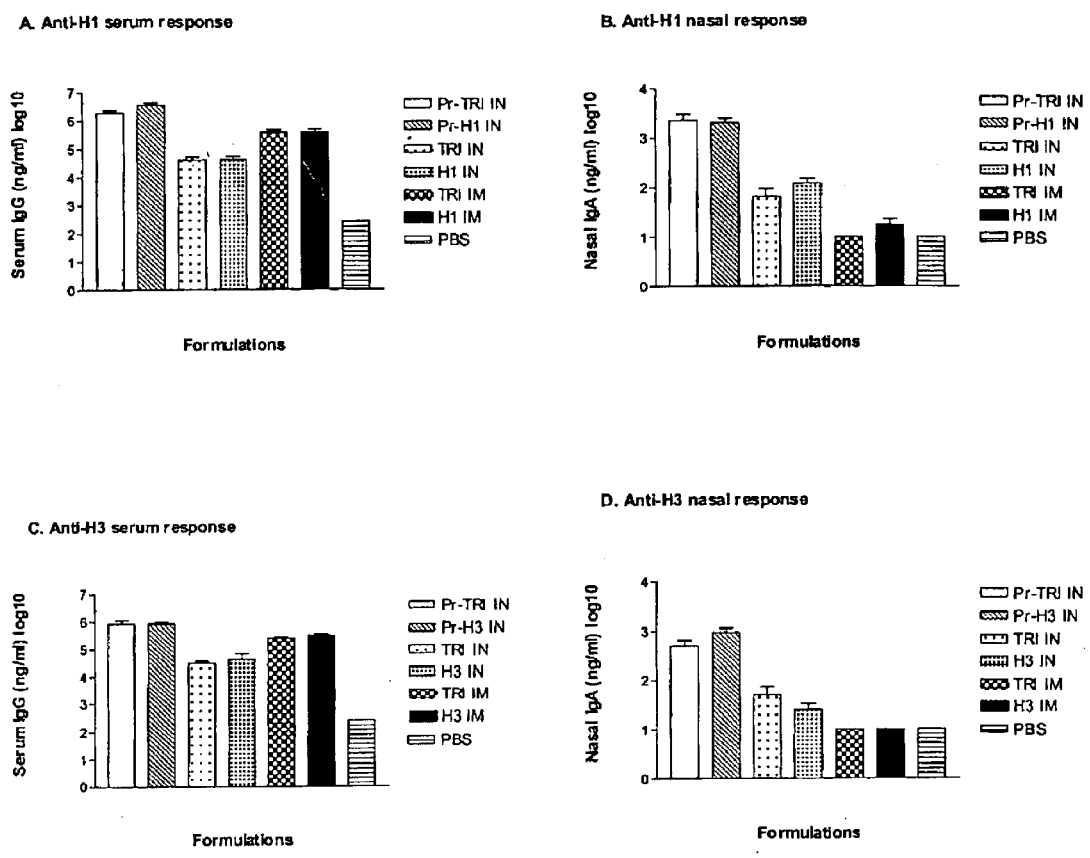
FIGS. 5A–5D are graphic representations of responses in serum and nasal mucosa to trivalent split influenza vaccines.

As shown in FIG. 4 and Table 3, the IgG1/IgG2a ratio was shifted from 14–20 (for Flu antigen alone) down to the 1–2 range when the vaccine contained proteosomes for both nasal and injected vaccines for split flu antigens; and from 6–60 to 1.7 for the baculo HA antigen. This shift of immunity from a Th2 to Th1 response was confirmed for the recombinant HA antigen by measuring cytokines produced after re-stimulating spleen cells from immunized animals with inactivated purified influenza virus. Briefly, Balb/c mice were euthanized 14 days after the second immunization and the spleens from 5 mice from each group were harvested and cells teased into a single cell suspension using a 100-μm nylon cell strainer (Becton Dickinson, N.J.). Spleen cells were cultured at 2.0×10$^6$ cells/ml (200 μl/well) in RPMI 1640 medium (Gibco BRL, Life technologies, Burlington, ON) containing 8% fetal bovine serum (heat-inactivated for 1 hr at 56° C.; Gibco BRL), 2 mM glutamine (Gibco BRL), 50 μM 2-mercaptoethanol (Sigma Chemical Co., St-Louis, Mo.) and 50 μg/ml gentamycin (Gibco BRL) with or without UV-inactivated X-113 (A/Texas/36/94 (H1N1) and X-31 (H3N2) reassortant); influenza virus (NIBSC, Hertfordshire, UK) in 96-well cell culture cluster (Corning, N.Y.). Cells were incubated for 72 hrs at 37° C. and supernatants harvested and frozen at −80° C. Murine cytokines levels were measured using sandwich ELISAs (OptEIA set) purchased from Pharmingen (San Diego, Calif.). according to manufacturer's instructions. Recombinant cytokine were used as standards.

Table 3. Nasal proteosome baculo HA vaccine shifts the immune response induced by rHA alone from a type 2 to a balanced Type 1/Type 2 immune response in mice

TABLE 3

Nasal proteosome baculo HA vaccine shifts the immune response induced by rHA alone from a Type 2 to a balanced Type 1/Type 2 immune response in mice

| | Pr-rHA (IN) | | | rHA (IN) | | | rHA (IM) | | |
|---|---|---|---|---|---|---|---|---|---|
| | G1/G2a* | INFγ** | IL-5** | G1/G2a | INFγ | IL-5 | G1/G2a | INFγ | IL-5 |
| | 1.7 | 4432 | 0 | 6.1 | 3769 | 390.5 | 60.1 | 6084 | 119.2 |

IgG1/IgG2a ratio's measured in sera pooled from 5 mice per group; **INFγ and IL-5 were determined in supernatants of mouse spleen cells re-stimulated as described in Example 11 with whole inactivated virus (1.25 ug/mL for IL-5 and 0.625 μg/mL for IFNγ) and are expressed in pg/mL of culture supernatant. Results are the means of triplicate cultures.

IgG1/IgG2a ratio's measured in sera pooled from 5 mice per group; **INFγ and IL-5 were determined in supernatants of mouse spleen cells re-stimulated as described in Example 11 with whole inactivated virus (1.25 μg/ml for IL-5 and 0.65 μg/ml for IFNγ)and are expressed in pg/mL of culture supernatant. Results are the means of triplicate cultures.

As shown in Table 3, the nasal proteosome HA vaccine induced the Th1 cytokine, interferon gamma without the Th2 cytokine IL-5; while the recombinant antigen administered by either the nasal or intramuscular route induced both IL-5 and interferon gamma. These data suggest that the nasal proteosome HA vaccine is creating a cytokine environment that favors the induction of other arms of immunity such as cytotoxic T cells. This may be advantageous since CTL are important for recovery from virus infection by eliminating virus from infected cells and for cross-protection against variant influenza strains.

EXAMPLE 11

Immunogenicity of Trivalent Formulations

Trivalent proteosome influenza vaccines were prepared using the procedure outlined in Example 3 using detergent split antigens from the A/Beijing/26/95 (H1N1), A/Sydney/05/97 (H3N2) and B/Yamanashi/166/98 sub-types of influenza virus. As shown in FIG. 5A–D for proteosome-flu vaccines made with each strain individually and combining them as a trivalent, strain specific serum IgG (FIG. 5A and C) and nasal IgA (FIG. 5B and D) responses are enhanced compared to their non-proteosome complexed controls. The immunoglobulin titers induced by the monovalent and trivalent proteosome-flu vaccines are not significantly different. Thus vaccines comprising multivalent influenza antigens induce serum and mucosal immune responses against each component, equivalent to that induced by the individual univalent vaccines.

Vaccines can also be prepared by combining the desired amounts of each individual antigen into a trivalent antigen pool and subsequently complexing the combined antigen pool to proteosomes to produce a multivalent proteosome-flu vaccine. Evidence for the particle size uniformity and consistency suitable for such a vaccine is shown in example 14 below. Evidence for the potency of such vaccines was found using the standard potency test for influenza vaccines viz. the SRID test described in example 3. Using the SRID test, substantial retention of potent HA was found for each of the three strains used in the multivalent vaccines made at either 8:1, 4:1 or 2:1 proteosome:HA ratios in both unfiltered samples as well as in samples filtered using 0.8 urn or 0.2 um filters. For example, using the 0.8 um filter, at each of three different proteosome:HA ratios (8:1, 4:1 and 2:1), 80% to 86% average retention of HA was found from the three influenza strains, H1N1, H3N2 and B in three trivalent vaccines. These data show that a multivalent vaccine can be made using this methodology.

EXAMPLE 12

Induction of Serum HAI and Nasal Wash sIgA in Humans

A Phase I dose escalating safety and immunogenicity study was performed in healthy sero-negative adults. Groups of patients (8 to 13 per group) received either 2 nasal doses of 7.5, 15 or 30 μg HA as a GMP grade proteosome-A/Beijing/262/95 vaccine or A/Beijing/262/95 antigen alone at 14 day intervals. HAI GMT were determined as described in Example 5. Secretory IgA specific for the antigen of interest in human nasal wash specimens were measured as follows. Nasal wash specimens were mixed vigorously and then concentrated four to five-fold in centrifugal concentrators with 50 kD cutoff membranes. Total secretory antibody (overwhelmingly dimeric secretory IgA, sIgA) was measured by single radial immunodiffusion in agarose containing antibody to human secretory piece using purified human sIgA standards. Antigen-specific sIgA was detected in a kinetic enzyme-linked immunosorbent assay (KELISA). Microtiter plates were coated with a predetermined concentration of antigen. After washing of the plates, samples of each concentrated nasal wash were placed in triplicate wells at a single dilution (selected in preliminary experiments to yield signals in the dynamic range of the assay for >95% of typical specimens). After incubation, the plates were washed and bound sIgA detected by sequential incubations with biotinylated goat anti-human secretory piece and avidin conjugated with horseradish peroxidase. Following a final wash, TMB substrate was added and optical density at 650 nm measured every 9 seconds for five minutes. A rate of color development (mOD/min) was calculated which, in the presence of excess detection reagents, is directly proportional to the concentration of sIgA bound to antigen. Results for each specimen are normalized to a standard sIgA concentration of 150 μg/mL by the formula:

Normalized KELISA rate=(specimen KELISA rate×150)÷specimen total sIgA conc.

The resultant normalized rates provide a linear (not geometric as, for example, titers) readout proportional to the amount of antigen-specific sIgA contained in a standard concentration of total sIgA in nasal fluid.

Figure 6:
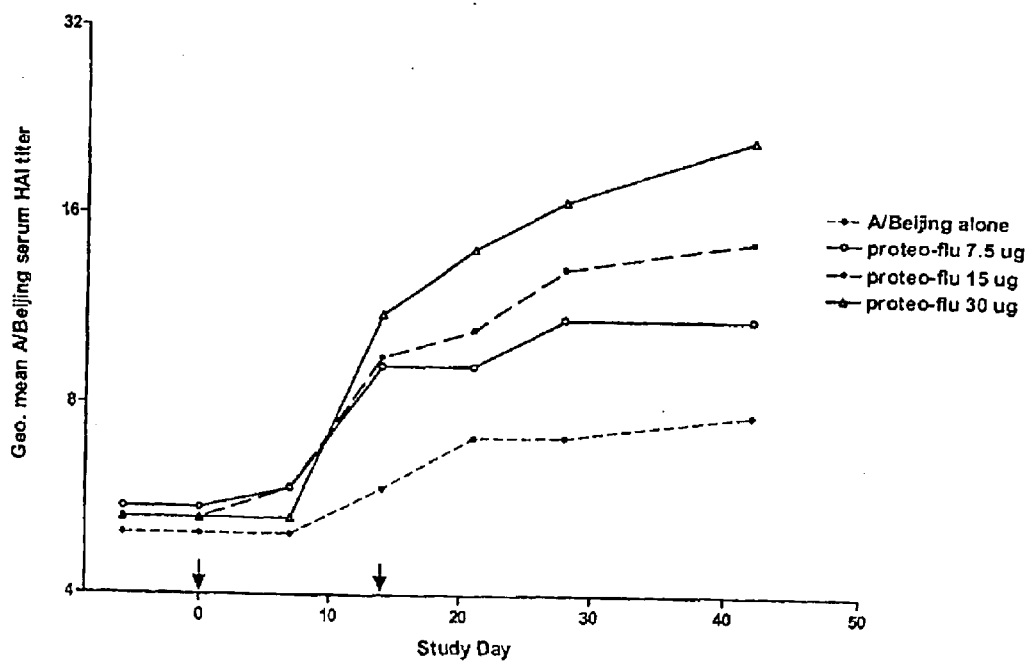
FIGS. 6A and 6B are graphs showing serum HAI and IgA signal in nasal washes, respectively, from humans immunized with the invention vaccines.
Figure 6:
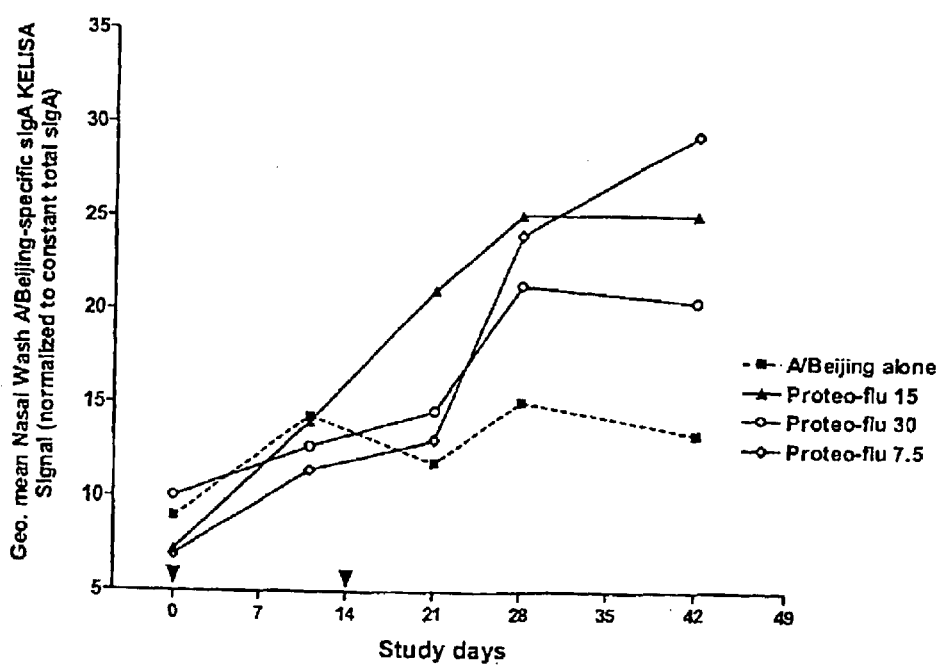
Figure 7:
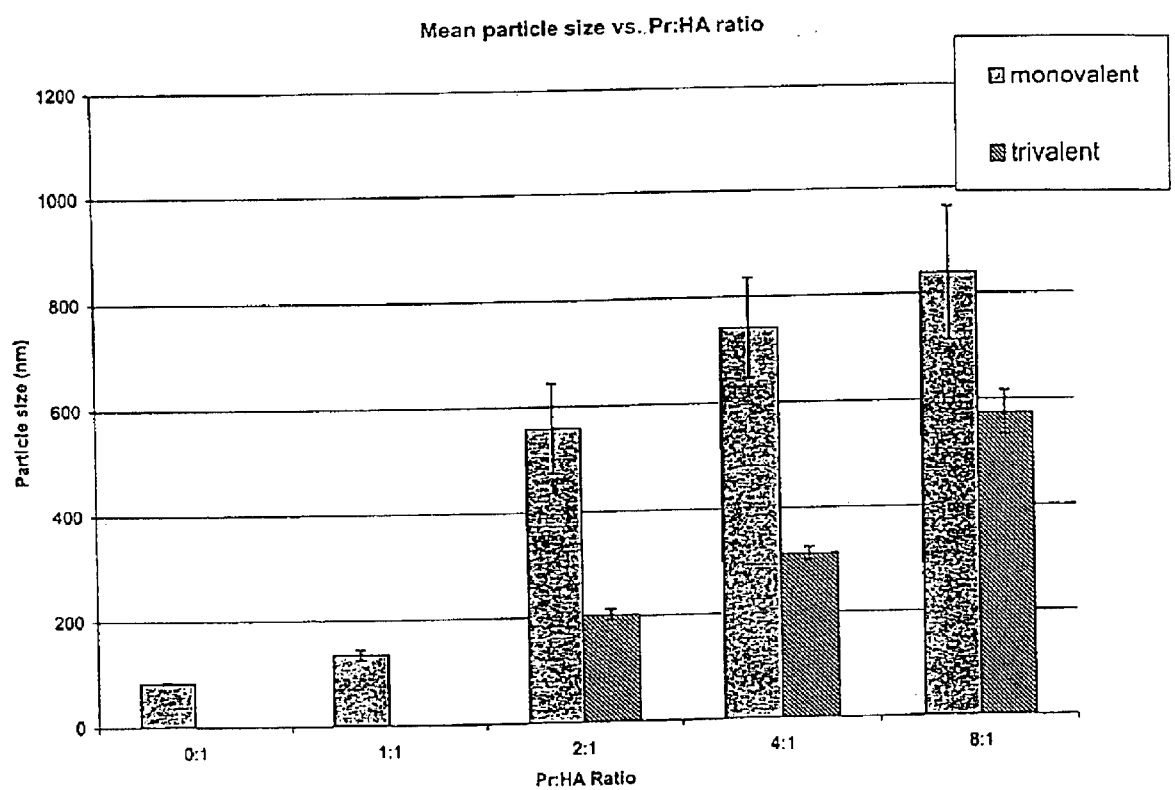
FIG. 7 shows a particle size analysis of proteosome-HA vaccine complexes.

The proteosome vaccine was well-tolerated at each antigen dose, allowing completion of the full dosing regime. Table 4 and FIG. 6A show the results for the GMT serum HAI titers and FIG. 6B shows nasal wash secretory IgA measurements at 42 days and 0 to 42 days respectively. Briefly, even in this profoundly seronegative population, approximately 50% of subjects had rises in the GMT serum HAI and most had post immunization titers of ≧40 that correlate with protection (Table 4). Furthermore, as shown by the time course of the serum HAI immune responses in FIG. 6A, strong responses were found in sera obtained from subjects immunized with each of the three dose levels (7.5, 15 or 30 μg) on day 14 before the second dose was administered indicating that one dose of vaccine may be sufficient in most individuals.

Table 4. Serum A/Beijing/262/95 HAI titers in humans following nasal immunization with proteosome-flu

TABLE 4

Serum A/Beijing/262/95 HAI titers in humans following nasal immunization with proteosome-flu

| Treatment Group | N | ≧4- fold rises on or before day 42 (%) | ≧40 HAI titer on or before day 42 (%) | HAI GMT day 42 |
|---|---|---|---|---|
| 15 μg A/Beijing | 8 | 1 (13) | 1 (13) | 7.7 |
| 7.5 μg proteo-flu | 8 | 2 (25) | 2 (25) | 10.9 |
| 15 μg proteo-flu | 13 | 6 (46) | 5 (38) | 14.5 |
| 30 μg proteo-flu | 13 | 7 (54) | 6 (46) | 21.1 |

In addition to serum HAI, the proteosome influenza vaccines induced significant rises in mucosal sIgA (≧2.9 fold) in more than 85% of the total subjects (FIG. 6B) including 75% of those individuals that received the lowest (7.5 μg) dose of vaccine. These data demonstrate the ability of the said invention to induce protective immune responses in humans. These responses are superior to those observed for CAV influenza vaccines in this age group which induced mucosal, but poor serum responses following nasal immunization.

The doses of proteosome-flu vaccine that give significant immune responses in humans are low and would not have been predicted from previous results where a 67 to 100-fold higher dose of antigen was required for significant systemic and mucosal responses following nasal immunization with proteosome shigella LPS vaccines (Ref. Abstract or manuscript submitted for publication).

EXAMPLE 13

SDS-PAGE Analysis for Proteosome-HA Vaccine Complexes Demonstrate Complexing of Proteosomes to Influenza-HA Antigen Uncomplexed proteosomes are insoluble in aqueous systems in the absence of surfactant; complexation with a soluble antigen solubilizes the proteosomes. By centrifuging the sample, the insoluble fraction is separated from the soluble fraction, and the identity of the contents of each is determined by SDS-PAGE. The presence of proteosome proteins in the supernatant with the soluble antigen is evidence of complexing with the antigen since in the absence of detergent or surfactant, the proteosome proteins are not soluble when not complexed by antigen. In order to determine the aggregation-state of an antigen-proteosome complex, a sample of the complex is spun in a centrifuge to pellet precipitated particles that may be present. The supernatant is transferred to another container and the pellet may be washed with TNS buffer. Both the supernatant and the pellet are then analyzed by SDS-PAGE with the non-complexed antigen run on the same gel as a reference. The gel is stained with Coomassie Blue stain, photographed, and re-stained with silver stain to enhanced sensitivity.

Non-complexed antigens are run as the reference standards. proteosome reference standard and molecular weight markers were: OMP001 reference standard: Mixture of GMP proteosome lots: 0175, 0566, 0621, 0621.

Molecular Weight Marker: Broad Range SDS-PAGE Standard

Proteosome-flu vaccines with complexes containing Pr:HA ratios ranging from 1:4 to 8:1 were made. Vaccines were tested for immunogenicity and for biochemical evidence of complexing as shown by the presence of proteosome proteins in the supernatants of samples centrifuged as described above. The data showed evidence of complexing of the proteosomes with the HA Flu antigen since characteristic bands of proteosome proteins were found in the SDS-PAGE gels in the supernatant with the HA influenza antigen. The presence of proteosomes in the supernatant is evidence of complex formation, since the proteosomes would otherwise be insoluble in the aqueous matrix. Surprisingly, proportionately more proteosomes were found in the supernatant when the preferred embodiment containing higher proteosome to HA ratios e.g. 4:1 (especially) or 8:1 were used whereas less proteosomes were found in the supernatant when lower ratios were used. Clearly, formulation at higher Pr:HA ratios (e.g. 4:1) allowed for more complexing and the lower ratios did not contain dose-limiting amounts of proteosomes that could be successfully complexed with the influenza antigen.

EXAMPLE 14

Particle Size Analysis of Proteosome-HA Vaccine Complexes Demonstrate Complexing of Proteosomes to Influenza-HA Antigen Number-weighted log analyzed particle size distributions for various ratios of Pr-HA complex were measured with a Brookhaven Instruments model 90 plus particle size analyzer. As shown in FIG. 8, monovalent and trivalent proteosome-flu vaccines with Pr:HA ratios greater than 1:1 contained particle size distributions that were significantly larger than that of the split flu HA control vaccine without proteosomes. Note that the range of sizes within each vaccine formulation was narrow and characteristic of the parameters of the vaccine formulation. Effective mean sizes may range from ca. 150 to 1,000 nm (with typical bell curve particle size distributions around these means) depending on the proteosome:HA ratio and characteristics of the specific antigen(s), as well as formulation parameters such as the type(s) of detergent(s) or membrane filter size used.

EXAMPLE 15

Demonstration of Complexing by Electron Microscopy

EM images of labeled proteosome-flu (monovalent A/Beijing) complex were obtained. A transmission electron microscope (TEM) image of the 4:1 Pr-HA vaccine complex, which was then labeled with anti-HA monoclonal antibody and protein A-gold shows that most of the HA is associated with the vesicular structures of the particles or particle aggregates of the complex vaccine. Few labeled sites are not associated with the particles.

A scanning electron microscope (SEM) image of the 4:1 Pr-HA complex incubated with the anti-HA monoclonal antibody followed by protein A-gold shows evidence of the three-dimensional structure of the vesicles. The apparent brightness of the gold particles is dependent on their orientation in the vesicle—gold particles on the back of the vesicle appear blurred and more faint than those on the front of the vesicle.

What is claimed is:

1. A method to prepare a vaccine effective against an influenza infection which method comprises:
   providing a mixture of at least one hemagglutinin (HA) antigen with a proteosome preparation in the presence of detergent, wherein the ratio of proteosomes to antigen is 2:1 or greater;
   removing detergent from said mixture by diafiltration or ultrafiltration to obtain a proteosome-antigen composition, and
   formulating said composition into a vaccine.

2. The method of claim 1 wherein said ratio is 2:1.

3. The method of claim 1 wherein said ratio is 4:1.

4. The method of claim 1 which includes more than one HA antigen.

5. A vaccine prepared by the method of any of claims 1–4.

6. The method of claim 1 wherein said detergent comprises more than one detergent.

7. A composition prepared as described in claim 1 which is filtered with a 0.2 or 0.8 $\mu$m filter.

8. An influenza vaccine which comprises at least one influenza hemagglutinin (HA) formulated with proteosomes in the substantial absence of detergent, wherein the formulation ratio of proteosomes to influenza HA is 2:1 or greater.

9. The vaccine of claim 8 wherein said HA and proteosomes are in the form of particles with a median size in the range of 150–1,000 nM as measured by light scattering.

10. A method to prepare a multivalent vaccine effective against an influenza infection which method comprises:
   providing a mixture of at least two hemagglutinin HA antigens to a proteosome preparation in the presence of detergent wherein the ratio of proteosomes to antigens is 2:1 or greater; and
   removing detergent from said mixture by diafiltration or ultrafiltration to obtain a proteosome-multivalent antigen composition, and
   formulating said composition into a vaccine.

11. The method of claim 8 wherein said ratio is 2:1.

12. The method of claim 8 wherein said ratio is 4:1.

13. A composition prepared as described in claim 8 which is filtered with a 0.2 or 0.8 μm filter.

14. An influenza vaccine which comprises at least one influenza hemagglutinin (HA) formulated with proteosomes in the substantial absence of detergent, wherein the formulation ratio of proteosomes to influenza HA is 2:1.

15. An influenza vaccine which comprises at least one influenza hemagglutinin (HA) formulated with proteosomes in the substantial absence of detergent, wherein the formulation ratio of proteosomes to influenza HA is 4:1.

16. An influenza vaccine which comprises at least three influenza hemagglutinin (HA) antigens formulated with proteosomes in the substantial absence of detergent, wherein the formulation ratio of proteosomes to influenza HA antigens is 2:1.

17. An influenza vaccine which comprises at least three influenza hemagglutinin (HA) antigens formulated with proteosomes in the substantial absence of detergent, wherein the formulation ratio of proteosomes to influenza HA antigens 134:1.

* * * * *

UNITED STATES PATENT AND TRADEMARK OFFICE
CERTIFICATE OF CORRECTION

PATENT NO. : 6,743,900 B2
DATED : June 1, 2004
INVENTOR(S) : David S. Burt et al.

It is certified that error appears in the above-identified patent and that said Letters Patent is hereby corrected as shown below:

Column 2,
Line 28, should read -- Despite the benefits described above ... --.

Column 7,
Line 13, should read -- ...the detergent-containing proteosome ... --.

Column 9,
Lines 49-50, should read -- ...showed optimal responses required that antigen doses... --.

Column 32,
Line 11, should read -- antigens is 4:1. --.

Signed and Sealed this

Fifteenth Day of November, 2005

JON W. DUDAS
*Director of the United States Patent and Trademark Office*